(12) United States Patent
Vroom

(10) Patent No.: US 11,607,056 B2
(45) Date of Patent: Mar. 21, 2023

(54) DIAPER CHANGING PAD AND PAD COVER

(71) Applicant: Kizua LLC, Arlington, VA (US)

(72) Inventor: Matthew L Vroom, San Francisco, CA (US)

(73) Assignee: KIZUA LLC, Arlington, VA (US)

( * ) Notice: Subject to any disclaimer, the term of this patent is extended or adjusted under 35 U.S.C. 154(b) by 0 days.

(21) Appl. No.: 16/831,450

(22) Filed: Mar. 26, 2020

(65) Prior Publication Data

US 2021/0315391 A1 Oct. 14, 2021

(51) Int. Cl.
| | | |
|---|---|---|
| A61F 13/15 | (2006.01) | |
| A47D 5/00 | (2006.01) | |
| A47D 15/00 | (2006.01) | |
| A61F 13/514 | (2006.01) | |

(52) U.S. Cl.
CPC ............... *A47D 5/00* (2013.01); *A47D 15/00* (2013.01); *A61F 13/514* (2013.01); *A61F 2013/51441* (2013.01)

(58) Field of Classification Search
CPC .............. A61F 13/5148; A61F 13/625; A61F 2013/15073; A61F 2013/51441; A61F 2013/51449; A61F 2013/51452; A61F 2013/5661
See application file for complete search history.

(56) References Cited

U.S. PATENT DOCUMENTS

| | | | |
|---|---|---|---|
| 4,894,060 A | 1/1990 | Nestegard | |
| 4,922,565 A | 5/1990 | Blake | |
| 4,979,520 A | 12/1990 | Boone, Jr. et al. | |
| 5,310,245 A | 5/1994 | Lyszczasz | |
| 5,554,146 A | 9/1996 | Niederhofer et al. | |
| 6,708,356 B1 | 3/2004 | LaValle | |
| 6,981,289 B2 | 1/2006 | Mueller et al. | |
| 7,003,832 B2 | 2/2006 | Wilson | |
| 7,111,344 B2 | 9/2006 | French | |
| 7,120,952 B1 | 10/2006 | Bass et al. | |
| 8,117,698 B1* | 2/2012 | Khaze Harry | ........... A47D 5/00 5/655 |
| 8,302,230 B1 | 11/2012 | Jarrett, Jr. et al. | |
| 8,338,658 B1* | 12/2012 | Kruger | ..................... A47D 5/00 604/356 |
| 8,572,782 B1 | 11/2013 | Amini | |
| 8,955,181 B2* | 2/2015 | Kelly | ................... A47D 15/008 5/655 |
| 9,032,572 B1 | 5/2015 | Leach | |
| 2002/0073480 A1 | 6/2002 | Phillips | |
| 2004/0033750 A1 | 2/2004 | Everett et al. | |
| 2014/0082847 A1 | 3/2014 | Thomas | |

(Continued)

OTHER PUBLICATIONS

Brochure from Minnesota Mining and Manufacturing Company titled "High Technology Hook" circa Apr. 2011 (2 pages).

(Continued)

*Primary Examiner* — Catharine L Anderson
(74) *Attorney, Agent, or Firm* — James R. Gourley; Carstens, Allen & Gourley, LLP

(57) ABSTRACT

A diaper changing pad and a cover for a diaper changing pad is provided. The diaper changing pad or diaper changing pad cover includes at least one region on its top surface that has male mechanical fastening structures that allow a clean diaper to be positioned in an open configuration, ready to be used in a diaper changing routine.

8 Claims, 3 Drawing Sheets

(56) References Cited

U.S. PATENT DOCUMENTS

| | | |
|---|---|---|
| 2015/0359355 A1 | 12/2015 | Rushing et al. |
| 2019/0350778 A1 | 11/2019 | Qi et al. |
| 2020/0069072 A1 | 3/2020 | Agcaoili et al. |
| 2020/0197560 A1 | 6/2020 | Buchalter |

OTHER PUBLICATIONS

Office Action dated Dec. 3, 2021 for U.S. Appl. No. 16/831,442 (30 pages).

* cited by examiner

DIAPER CHANGING PAD AND PAD COVER

BACKGROUND OF THE INVENTION

Technical Field

The present invention relates to an apparatus for changing a baby diaper.

Description of Related Art

When a baby's diaper becomes soiled, the diaper is typically changed by laying the baby down on a surface, removing the soiled diaper, and replacing it with a clean one. A popular surface used in many households is a concave pad that helps prevent a baby from rolling off the surface during the diaper change routine. These pads are typically made of a soft, padded material that is comfortable for a baby to lay on. There are also washable covers for these pads, also made of a soft, flexible material that is comfortable for a baby's skin.

SUMMARY OF THE INVENTION

In one embodiment, a diaper changing pad comprises at least one male mechanical fastening element region on a top surface of the diaper changing pad. In another embodiment, in combination with any other embodiment or combination of embodiments, the diaper changing pad further comprises a top half and a bottom half, wherein the top half and bottom half are separated by a widthwise axis, wherein the widthwise axis is perpendicular to a lengthwise axis, wherein the at least one male mechanical fastening element region is located on the bottom half of the pad. In another embodiment, in combination with any other embodiment or combination of embodiments, the diaper changing pad comprises three separate male mechanical fastening element regions. In another embodiment, in combination with any other embodiment or combination of embodiments, of the diaper changing pad, each male mechanical fastening element region comprises a center point, further wherein the center points are arranged in isosceles or equilateral triangle arrangement. In another embodiment, in combination with any other embodiment or combination of embodiments, of the diaper changing pad, the male mechanical fastening element region includes a plurality of male mechanical fastening structures, wherein each male mechanical fastening structure comprises a stem and a fiber engagement element. In another embodiment, in combination with any other embodiment or combination of embodiments, of the diaper changing pad, the male mechanical fastening structures are engageable with a fibrous web structure of a diaper backsheet. In another embodiment, in combination with any other embodiment or combination of embodiments, of the diaper changing pad, the at least one male mechanical fastening element region is symmetrical about a lengthwise axis.

In one embodiment, a diaper changing pad cover comprises at least one male mechanical fastening element region on a top surface of the diaper changing pad cover; and an elastic rim opposite the top surface. In another embodiment, in combination with any other embodiment or combination of embodiments, the diaper changing pad cover further comprises a top half and a bottom half, wherein the top half and bottom half are separated by a widthwise axis, wherein the widthwise axis is perpendicular to a lengthwise axis, wherein the at least one male mechanical fastening element region is located on the bottom half of the cover. In another embodiment, in combination with any other embodiment or combination of embodiments, the diaper changing pad cover comprises three separate male mechanical fastening element regions. In another embodiment, in combination with any other embodiment or combination of embodiments, of the diaper changing pad cover, each male mechanical fastening element region comprises a center point, further wherein the center points are arranged in isosceles or equilateral triangle arrangement. In another embodiment, in combination with any other embodiment or combination of embodiments, of the diaper changing pad cover, the male mechanical fastening element region includes a plurality of male mechanical fastening structures, wherein each male mechanical fastening structure comprises a stem and a fiber engagement element. In another embodiment, in combination with any other embodiment or combination of embodiments, of the diaper changing pad cover, the male mechanical fastening structures are engageable with a fibrous web structure of a diaper backsheet. In another embodiment, in combination with any other embodiment or combination of embodiments, the diaper changing pad cover further comprises a protective cover for each male mechanical fastening element region. In another embodiment, in combination with any other embodiment or combination of embodiments, of the diaper changing pad cover, the at least one male mechanical fastening element region is symmetrical about a lengthwise axis.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

The present invention relates to an apparatus for improving the process for changing a baby's soiled diaper and replacing it with a clean one. In one embodiment, the apparatus is a diaper changing pad with a male mechanical fastening element region that is configured to allow a user to position a clean diaper on the diaper changing pad in an open and ready position before the baby is placed on the changing pad. The male mechanical fastening element region holds the diaper in place, and holds the diaper in open position, thereby freeing the hands of the caregiver to devote full attention to the baby, instead of requiring the caregiver to use one hand to hold the clean diaper in the open and ready position. Thus, the invention may have special significance to caregivers with disabilities, or compromised upper limb dexterity or fine motor skills. In another embodiment, the apparatus is a cover for a diaper changing pad that has a male mechanical fastening element region configured to allow for the same improved diaper changing procedure described above. Any feature or embodiment described herein for a diaper changing pad applies equally to a diaper changing pad cover because once a diaper changing pad cover is placed over a diaper changing pad, the diaper changing pad plus cover will be the equivalent of a diaper changing pad described herein.

Figure 1:
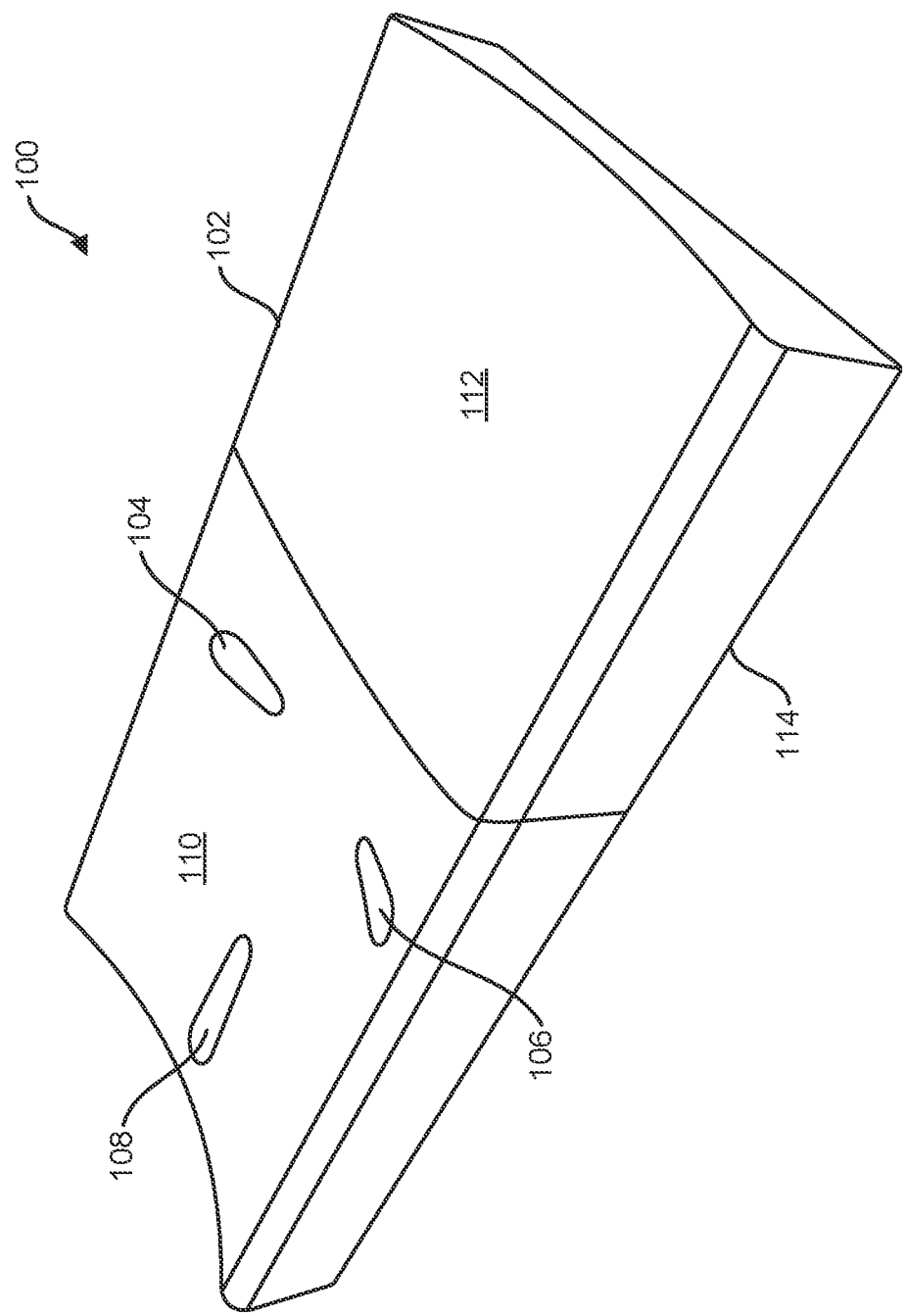
FIG. 1 is a perspective view of one embodiment of the present invention.

FIG. 1 is a perspective view of one embodiment of the present invention. In this exemplary embodiment, the diaper changing pad or cover 100 comprises three separate and distinct male mechanical fastening element regions 104, 106, 108 on a top surface 102. The remainder of the diaper changing pad or cover 100 is made of a soft flexible cloth or cloth-like material, such as cotton or nylon, that is comfortable on the skin of a baby.

In the embodiment shown in FIG. 1, the diaper changing pad or cover 100 comprises a top half 112 and a bottom half 110. The top half 112 of the diaper changing pad or cover is typically the half of the diaper changing pad or cover that corresponds with the head of the baby that is laid on the diaper changing pad or cover during the diaper changing routine. The bottom half 110 of the diaper changing pad or cover is the half opposite the top half, or the half of the diaper changing pad or cover corresponding to the feet of the baby that is laid on the diaper changing pad or cover during the diaper changing routine. As used herein, the boundary between the top half 112 and bottom half 110 of the diaper changing pad or cover is a widthwise axis, wherein the widthwise axis runs substantially perpendicular to a lengthwise axis.

In the embodiment shown in FIG. 1, the male mechanical fastening element regions 104, 106, 108 are located on the bottom half 110 of the diaper changing pad or cover, which is where the clean diaper is advantageously positioned during the diaper changing routine. Further, there is no male mechanical fastening element region on the top half 112 of the diaper changing pad or cover because the material used to make the remainder of the cover is typically softer and more comfortable for a baby's skin than the male mechanical fastening element region.

In the embodiment shown in FIG. 1, the male mechanical fastening element regions 104, 106, 108 are arranged symmetrically around a lengthwise axis. In particular, each of the male mechanical fastening element regions has a center point, and the center points of each male mechanical fastening element region are arranged in isosceles or equilateral triangle arrangement. Preferably, the height of the isosceles or equilateral triangle includes or is parallel with the lengthwise axis of the diaper changing pad or cover.

Figure 2:
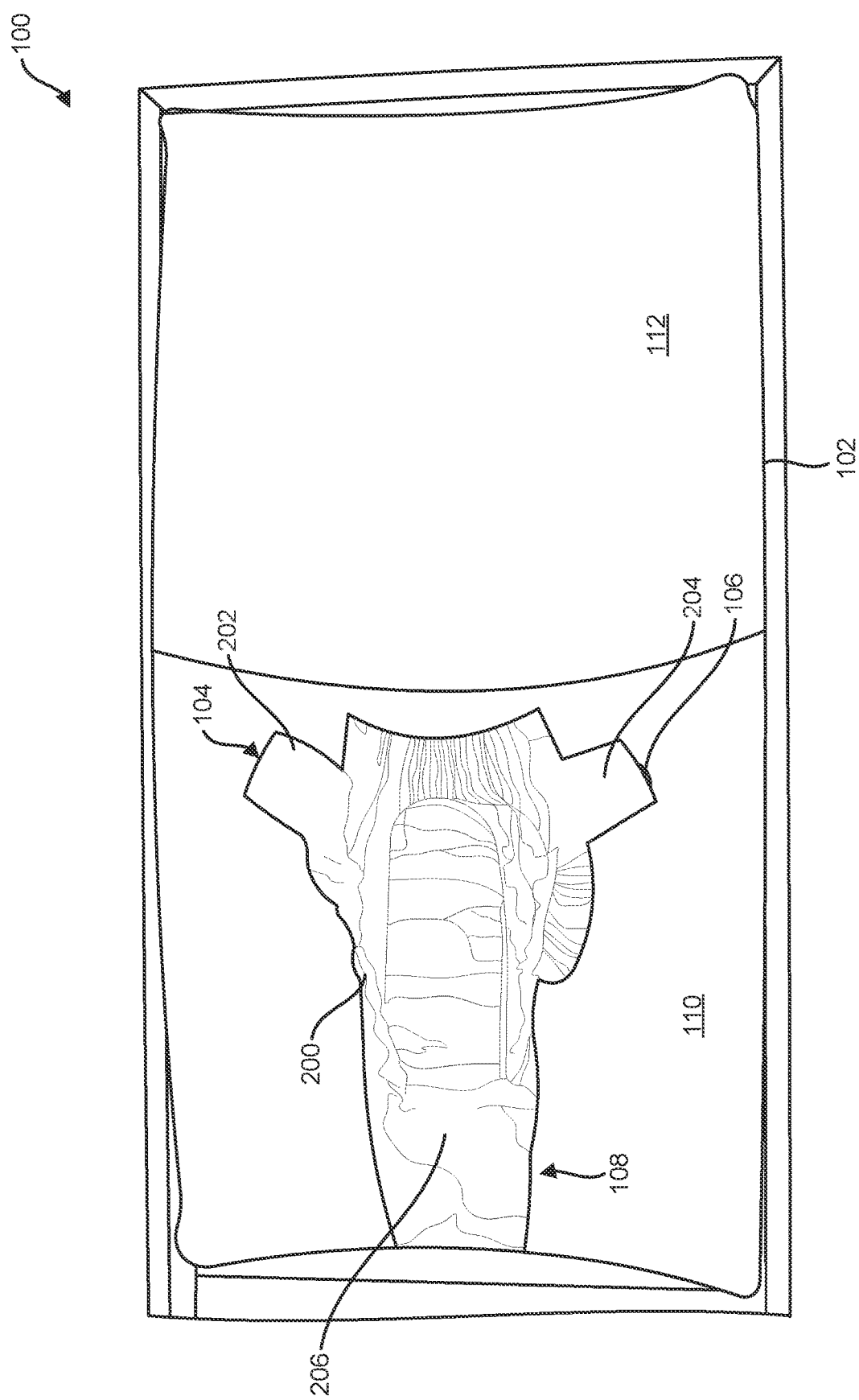
FIG. 2 is a top plan view of one embodiment of the present invention with a clean diaper attached to the invention and ready for use.

FIG. 2 shows a top elevation view of the diaper changing pad or cover 100 shown in FIG. 1 with a clean diaper 200 attached to it. The diaper has a first tab 202 attached to male mechanical fastening element region 104, and a second tab 204 attached to male mechanical fastening element region 106. The diaper also has a frontal segment 206 attached to male mechanical fastening element region 108. Because the diaper is attached to the diaper changing pad or cover at these three points, the diaper is held securely in place and open, ready to be used in the diaper changing routine. This ability to hold a diaper open and ready is important because disposable diapers are commonly sold in multi-packs that contain a large number of diapers folded and compressed against one another. Consequently, such diapers do not readily stay open when they are removed from a package and opened by a caregiver. The present invention is a vast improvement on the prior art because it will hold a diaper open and in place during the diaper changing routine. Further, the male mechanical fastening element region, described in more detail below, provides a superficial, temporary, or removable attachment to the diaper, so that it can be easily peeled away from the male mechanical fastening element region whenever it is convenient to do so during the diaper changing routine.

Figure 3:
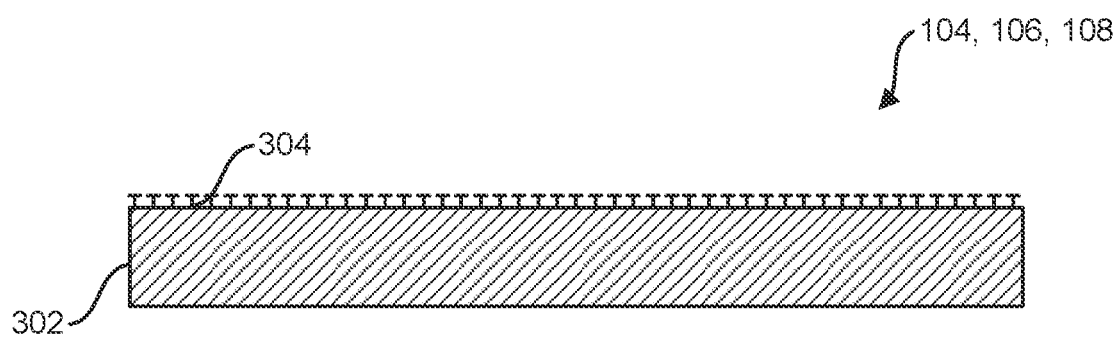
FIG. 3 is a cross-sectional view of one example of the male mechanical fastening element region of one embodiment of the present invention.

FIG. 3 is a cross-sectional view showing one example of a male mechanical fastening element region 104, 106, or 108. As shown therein, generally the male mechanical fastening element region comprises a plurality of male mechanical fastening structures 304 protruding from a base material 302. In the example shown in FIG. 3, the male mechanical fastening structures 304 have a T-shaped cross section. However, other variations are possible, such as various curved "hook" shaped structures.

Generally, the male mechanical fastening structures are engageable with a fibrous web structure like those commonly found on the exterior surface of commercially available disposable diapers. Commercially available disposable diapers commonly include a backsheet on the outside of a diaper that comprises a nonwoven or woven, stitch bonded, knitted or the like, fibrous web. The fibrous web is engageable with male mechanical fastening structures found on the fastening tabs of diapers (for example, 202 and 204 shown in FIG. 2). Typically, the fibrous web structure of the diaper's backsheet will have sufficient fiber loft, fiber spacing, and fiber size to allow penetration by the male mechanical fastening structures, but sufficient fiber density and size so that a substantial portion of the mechanical fastening structures engage fibers of the web, thereby removably adhering to the fibrous web. The fibrous web structure allows the fastening tabs to be attached to almost any location on the backsheet of a diaper, which further allows the shape of the diaper to fit babies having different body shapes.

A general male mechanical fastening structure shape includes a stem portion and a fiber engagement element. In the embodiment shown in FIG. 3, the vertical portion of the T shape is the stem portion, and the horizontal upper portion extending laterally from the stem of the T is the fiber engagement element. The stem portion is can be generally narrower than the fiber engagement element over its full length and has no outward protrusions or fiber engagement structures. Generally, the stem portion can have straight sides or taper inwardly from the base material face to the fiber engagement element. The fiber engagement element can be in the shape of a mushroom, a circular disk, a J-hook, a double J-hook, a bilobal (i.e. T-shaped), multi-lobal, or any other suitable shape capable of engaging a fibrous web. In one embodiment, the male mechanical fastening structure, as measured from stem to outermost surface of the fiber engagement element, generally is at least 75 microns in length, and preferably 100 to 400 microns in length. Suitable materials for forming the male mechanical fastening structures include thermoplastic polymers, such as polyester, polyolefins, polypropylene, vinyl, nylons, and the like. In addition to considerations regarding the level of engagement between the diaper backsheet and male mechanical fastening structures, the shape, size, and materials used to make the male mechanical fastening structures are also influenced by the level of comfort provided to a baby's skin during the diaper changing routine.

Referring back to FIG. 1, the number, shape, and location of male mechanical fastening element regions is not limiting on the present invention. Preferably, the male mechanical fastening element region will be sized, shaped and configured to allow a diaper to be positioned on the diaper changing pad or cover in open position and ready for the diaper changing routine. Examples of such a size and shape can be determined by one skilled in the art after reading the disclosure herein. For example, instead of providing three distinct male mechanical fastening element regions, the diaper changing pad or cover could include a single male mechanical fastening element region that is generally T-shaped, such that male mechanical fastening region runs continuously from region 104 to 106, and then down to region 108. Alternatively, a larger number of smaller male mechanical fastening element regions could be positioned on the bottom half of the diaper changing pad or cover to allow for a wide variety of diaper positions.

Additionally, the male mechanical fastening element regions can be constructed as a part of the diaper changing pad or cover by adhering one or more sections of male mechanical fastening material to the diaper changing pad or cover using a number of different techniques. Preferably, the male mechanical fastening material is sewn into or onto the flexible cloth or cloth-like material that makes up the remainder of the outer surface of the diaper changing pad or cover. Also, preferably the male mechanical fastening element regions will be flush with the top surface of the diaper changing pad or cover so that the baby's skin will not experience any discomfort if it comes into contact with the male mechanical fastening element region. The male mechanical fastening element regions may also be embroidered around the edges to prevent any sharp edges on the material used to make the male mechanical fastening element regions from contacting a baby's skin. Usually, during the diaper changing routine, the clean diaper will completely cover the male mechanical fastening element regions and prevent them from contacting the baby's skin, but some use cases may involve contact with the baby's skin.

For the diaper changing pad cover embodiment, typically the diaper changing pad cover will comprise an elastic rim around the base 114, which holds the diaper changing pad cover onto the diaper changing pad.

Additionally, because the diaper changing pad cover is typically more easily washable than the diaper changing pad, it is anticipated that the diaper changing pad covers will be washed more frequently. Another optional feature of the present invention is a male mechanical fastening element region cover, which serves to protect the male mechanical fastening element region from damage during a wash cycle and from adhering to or damaging other clothing items present with the cover in the wash cycle. Damage to the small male mechanical fastening structures can occur in a number of ways. Hot water can soften the male mechanical fastening structures and make them more likely to suffer impact damage during washing or drying. Fibers from cloth materials present with the cover (even perhaps from the cloth used on other portions of the cover) may become lodged within the male mechanical fastening element region structure, thereby degrading the adhesive qualities of the male mechanical fastening element region. Damage could also occur during shipment of new diaper changing pad covers. Further, the adhesive qualities of the male mechanical fastening element regions could cause difficulties in the manufacturing and packaging of the diaper changing pads or covers. Consequently, in one embodiment, the male mechanical fastening element region is provided with a protective cover that attaches to the male mechanical fastening element region during shipping or during a wash cycle. In one embodiment, the protective cover is comprised of a material very similar to the male mechanical fastening element region structure shown in FIG. 3, with male mechanical fastening structures sized and structured to mesh with the male mechanical fastening structures found in the male mechanical fastening element region on the diaper changing pad cover. Alternatively, the protective cover is comprised of a fibrous material that engages well with the male mechanical fastening element region, but made of fibers that do not easily dislodge and remain entangled within the male mechanical fastening element structures, thereby degrading the adhesive qualities of the male mechanical fastening element region.

It will now be evident to those skilled in the art that there has been described herein a diaper changing pad or diaper changing pad cover having a male mechanical fastening element region that allows for a safer, more efficient diaper changing routine. Although the invention hereof has been described by way of preferred embodiments, it will be evident that other adaptations and modifications can be employed without departing from the spirit and scope thereof. The terms and expressions employed herein have been used as terms of description and not of limitation; and thus, there is no intent of excluding equivalents, but on the contrary it is intended to cover any and all equivalents that may be employed without departing from the spirit and scope of the invention. In sum, while this invention has been particularly shown and described with reference to a preferred embodiment, it will be understood by those skilled in the art that various changes, in form and detail may be made therein without departing from the spirit and scope of the invention.

What is claimed is:

1. A diaper changing pad cover consisting essentially of:
   a flexible cloth or cloth-like material having at least one male mechanical fastening element region on a top surface of the flexible cloth or cloth-like material diaper changing pad cover;
   an elastic rim opposite the top surface, wherein the diaper changing pad cover is made of a flexible cloth or cloth-like material.

2. The diaper changing pad cover of claim 1 further comprising:
   a top half and a bottom half, wherein the top half and bottom half are separated by a widthwise axis, wherein the widthwise axis is perpendicular to a lengthwise axis, wherein the at least one male mechanical fastening element region is located on the bottom half of the cover.

3. The diaper changing pad cover of claim 1 comprising three separate male mechanical fastening element regions.

4. The diaper changing pad cover of claim 3 wherein each male mechanical fastening element region comprises a center point, further wherein the center points are arranged in isosceles or equilateral triangle arrangement.

5. The diaper changing pad cover of claim 1 wherein the male mechanical fastening element region includes a plurality of male mechanical fastening structures, wherein each male mechanical fastening structure comprises a stem and a fiber engagement element.

6. The diaper changing pad cover of claim 1 wherein the male mechanical fastening structures are engageable with a fibrous web structure of a diaper backsheet.

7. The diaper changing pad cover of claim 1 further comprising a protective cover for each male mechanical fastening element region.

8. The diaper changing pad cover of claim 1 wherein the at least one male mechanical fastening element region is symmetrical about a lengthwise axis.

* * * * *